(12) United States Patent
Morimoto et al.

(10) Patent No.: US 12,016,758 B2
(45) Date of Patent: Jun. 25, 2024

(54) ABSORBENT ARTICLE WITH LEG GASKETING SYSTEM

(71) Applicant: The Procter & Gamble Company, Cincinnati, OH (US)

(72) Inventors: Koichi Morimoto, Beijing (CN); Mengmeng Zhang, Beijing (CN); Natalia Nikolaewna Gaiko, Kronberg (DE); Christine Elisabeth Schober, Eschborn (DE); Sarah Zitzer, Giessen (DE); Petra Ballenberger, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 154 days.

(21) Appl. No.: 17/683,410

(22) Filed: Mar. 1, 2022

(65) Prior Publication Data

US 2022/0280353 A1    Sep. 8, 2022

(30) Foreign Application Priority Data

Mar. 4, 2021 (WO) ................ PCT/CN2021/079060
Sep. 9, 2021 (WO) ................ PCT/CN2021/117434

(51) Int. Cl.
*A61F 13/49* (2006.01)
*A61F 13/514* (2006.01)

(52) U.S. Cl.
CPC .. *A61F 13/49017* (2013.01); *A61F 13/49011* (2013.01); *A61F 13/51474* (2013.01); *A61F 2013/49093* (2013.01)

(58) Field of Classification Search
CPC .......... A61F 13/49009; A61F 13/49011; A61F 13/49014; A61F 13/49017;
(Continued)

(56) References Cited

U.S. PATENT DOCUMENTS 10,492,962 B2    12/2019    Greening, II et al.
2008/0255532 A1   10/2008   Schroer
(Continued)

OTHER PUBLICATIONS

All Office Actions; U.S. Appl. No. 18/229,316, filed Aug. 2, 2023.
(Continued)

*Primary Examiner* — Leslie A Lopez
*Assistant Examiner* — Seth Han
(74) *Attorney, Agent, or Firm* — Charles R. Matson

(57) ABSTRACT

Disclosed is an absorbent article comprising a core chassis and a leg gasketing system comprising a pair of wearer facing cuff regions comprising an inner cuff sealing and inner cuff free edge positioned inward from the inner cuff sealing, wherein the inner cuff sealing bonds the cuff material and a topsheet, and an inner cuff elastic element is disposed adjacent the inner cuff free edge; a pair of garment facing cuff regions formed by inwardly extending the cuff material over a garment facing side of the core chassis, and a pair of outer cuff elastic elements disposed on wearer facing cuff regions or garment facing cuff regions; and wherein the absorbent article has a Worn Leg Opening (WLO) of from about 300 mm to about 450 mm, a Minimum Leg Opening (MLO) of from about 225 mm to about 300 mm, and a ratio of WLO/MLO of from about 1.5 to about 1.7.

13 Claims, 7 Drawing Sheets

(58) Field of Classification Search
CPC .. A61F 2013/49028; A61F 2013/49025; A61F 13/49; A61F 2013/49092; A61F 2013/49093; A61F 13/49413; A61F 13/49406; A61F 13/494; A61F 13/49453
See application file for complete search history.

(56) References Cited

U.S. PATENT DOCUMENTS

| | | | |
|---|---|---|---|
| 2011/0071488 A1* | 3/2011 | Kuwano | A61F 13/49011 604/385.3 |
| 2011/0245792 A1 | 10/2011 | Oconnell | |
| 2014/0257228 A1* | 9/2014 | Wang | A61F 13/505 604/385.14 |
| 2015/0065982 A1 | 3/2015 | Hamilton | |
| 2016/0058625 A1* | 3/2016 | Morimoto | A61F 13/496 604/385.27 |
| 2018/0168885 A1* | 6/2018 | Zink, II | A61F 13/15739 |
| 2018/0333313 A1 | 11/2018 | Lavon et al. | |
| 2020/0000648 A1* | 1/2020 | Kleuskens | A61F 13/4902 |
| 2020/0085644 A1 | 3/2020 | Tong et al. | |
| 2020/0107972 A1 | 4/2020 | Raycheck et al. | |
| 2022/0280354 A1 | 9/2022 | Zhang et al. | |

OTHER PUBLICATIONS

U.S. Appl. No. 18/229,316, filed Aug. 2, 2023, to Koichi Morimoto et al.
AA01485FQ PCT Search Report and Written Opinion for PCT/CN2021/117434 dated Jan. 28, 2022, 11 pages.
All Office Actions; U.S. Appl. No. 17/683,432, filed Mar. 1, 2022.

* cited by examiner

ABSORBENT ARTICLE WITH LEG GASKETING SYSTEM

CROSS REFERENCE TO RELATED APPLICATIONS

This application claims priority to Chinese PCT Patent Application No. PCT/CN2021/117434, filed on Sep. 9, 2021, and to Chinese PCT Patent Application No. PCT/CN2021/079060, filed on Mar. 4, 2021, both of which are incorporated by reference herein.

FIELD OF INVENTION

This invention relates to absorbent articles such as diapers having a leg gasketing system with improved softness, coverage, and leakage prevention.

BACKGROUND OF THE INVENTION

Absorbent articles having a leg gasketing system comprising an inner leg cuff and an outer leg cuff are well known in the art. The usage of the inner leg cuff is mainly to prevent leakage of bodily exudates and the outer leg cuff is mainly for providing a covering over the inner leg cuff to minimize the visibility of exudates through the inner leg cuff and to provide a secondary means to capture bodily exudates should they breach the inner leg cuff. The inner leg cuff is typically made using substantially liquid impervious non-woven material and inner leg elastic element disposed at the free edge of the inner leg cuff extending in the longitudinal direction, and disposed on the body-facing surface of the absorbent article to provide a sealing directly against the wearer's skin. The outer leg cuff is typically made using similar nonwoven material as the inner leg cuff and disposed laterally outside the inner leg cuff. The outer leg cuff may also have an outer leg elastic element extending in the longitudinal direction. The forces provided by the inner leg elastic element and outer leg elastic element must be carefully selected in order to provide the expected sealing, while also avoid red marks created on the wearer's skin during wearer, and avoid creation of inadvertent forces pulling away the remainder of the absorbent article from the wearer's skin. Further, in that the outer leg cuff may form the longitudinally extending side edges of the absorbent article, the appearance of the outer leg cuff may influence the aesthetic impression of the entire absorbent article. Current products on the market are not completely satisfactory in meeting all of the various needs expected of a leg gasketing system.

Based on the foregoing, there is a need for an absorbent article having a leg gasketing system that has improved tactile softness and coverage, while maintaining the performance of leakage protection. There is further a need for manufacturing such a wearable article in a reliable and economical manner.

SUMMARY OF THE INVENTION

The present invention is directed to an absorbent article having a skin facing side, a garment facing side, a longitudinal axis, a transverse axis, a pair of longitudinally extending side edges, and a pair of transversely extending end edges, the absorbent article comprising an absorbent body, a front belt joined to the front side of the absorbent body, a back belt joined to the back side of the absorbent body, and the transverse edges of the front belt and the back belt are joined by a seam to form a waist opening and two leg openings,

- each front belt and back belt formed by a plurality of elastic bodies running in the transverse direction sandwiched between an inner sheet and an outer sheet;
- the absorbent body comprising:
  1) a core chassis comprising:
     1a) a liquid permeable topsheet;
     1b) a liquid impermeable backsheet;
     1c) an absorbent core disposed between the topsheet and the backsheet, the absorbent core having a smaller dimension than the backsheet in both the longitudinal direction and the transverse direction;
     1d) an outer cover disposed on the garment facing side of the backsheet, the outer cover having a greater dimension than the absorbent core in the transverse direction, and the same or smaller dimension than the backsheet in both the longitudinal direction and the transverse direction; and
     1e) a pair of core side regions defined as the region between the respective absorbent core side edges and the backsheet side edges; and
  2) a leg gasketing system made by a pair of water impermeable cuff material disposed laterally outside and wrapping the pair of sides edges of the core chassis, the leg gasketing system comprising;
     2a) a pair of wearer facing cuff regions formed by inwardly extending the cuff material over the wearer facing side of the core chassis; each of the pair of wearer facing cuff regions comprise a longitudinally extending inner cuff sealing and a longitudinally extending inner cuff free edge positioned inward from the inner cuff sealing, wherein the inner cuff sealing bonds the cuff material and the topsheet, and an inner cuff elastic element is disposed adjacent the inner cuff free edge;
     2b) a pair of garment facing cuff regions formed by inwardly extending the cuff material over the garment facing side of the core chassis, and
     2c) a pair of outer cuff elastic elements disposed on the wearer facing cuff regions or the garment facing cuff regions, each outer cuff elastic element disposed so as to superpose the core side regions and so as to superpose the inner cuff sealings or outward thereof; and
- wherein the absorbent article has a Worn Leg Opening (WLO) of from about 300 mm to about 450 mm, a Minimum Leg Opening (MLO) of from about 225 mm to about 300 mm, and a ratio of WLO/MLO of from about 1.5 to about 1.7.

DEFINITIONS

Figure 1:
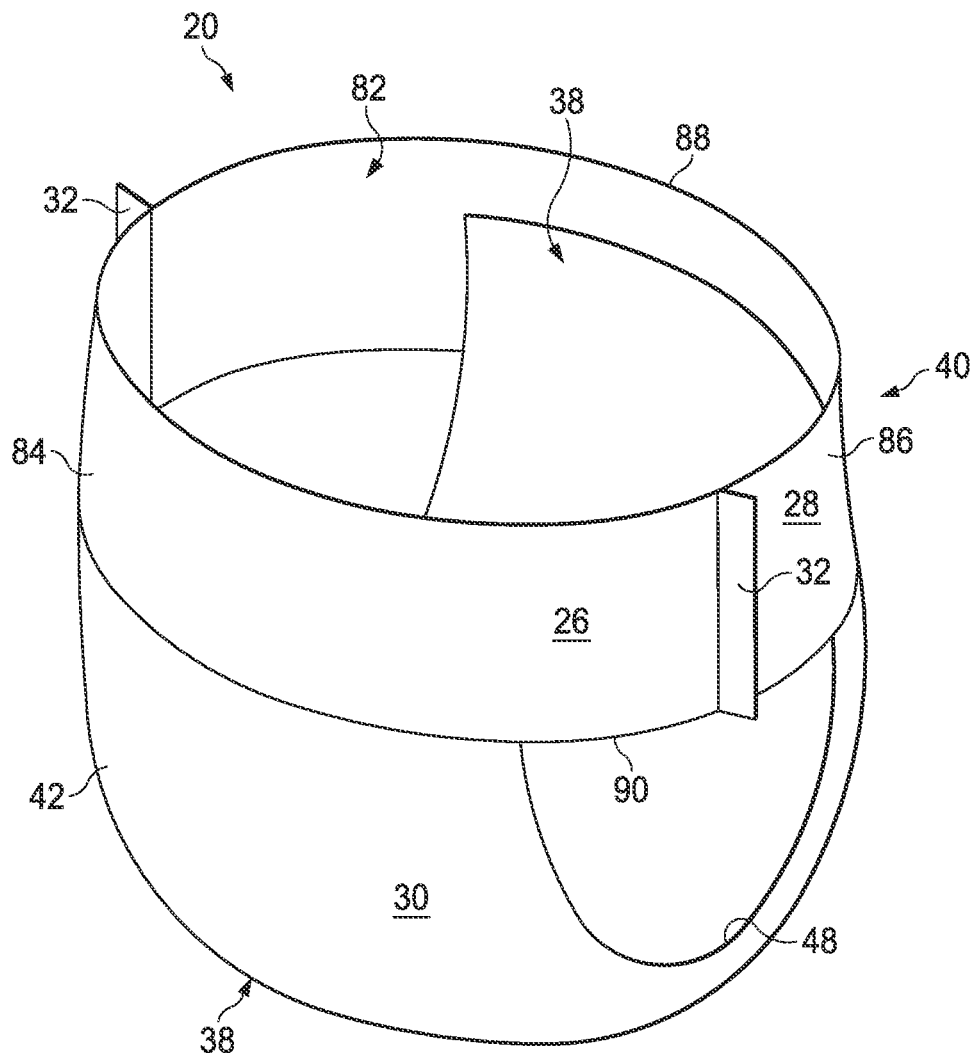
FIG. 1 is a perspective view of an exemplary absorbent article of the present invention.

As used herein, the following terms shall have the meaning specified thereafter:

"Absorbent article" refers to articles of wear which may be in the form of taped type diapers, pant type diapers, incontinent briefs, feminine hygiene garments, and the like. The "absorbent article" may be so configured to absorb and contain various exudates such as urine, feces, and menses discharged from the body.

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Inward" and "outward" refer respectively to the position closer or farther relative to the transverse center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION OF THE INVENTION

Referring to FIG. 1, the present invention relates to absorbent articles comprising an absorbent body (38), a front belt (84) joined to the front side of the absorbent body (38), a back belt (86) joined to the back side of the absorbent body (38), the absorbent body (38) comprising a core chassis (61) and a leg gasketing system (100), the leg gasketing system (100) providing improved softness, coverage, and leakage prevention. The front and back belts (84, 86) form an elastic belt (40) extending transversely from the front and back regions (26, 28) of the absorbent body (38) and seamed with each other at the pair of transverse edges as side seams (32).

Figure 2A:
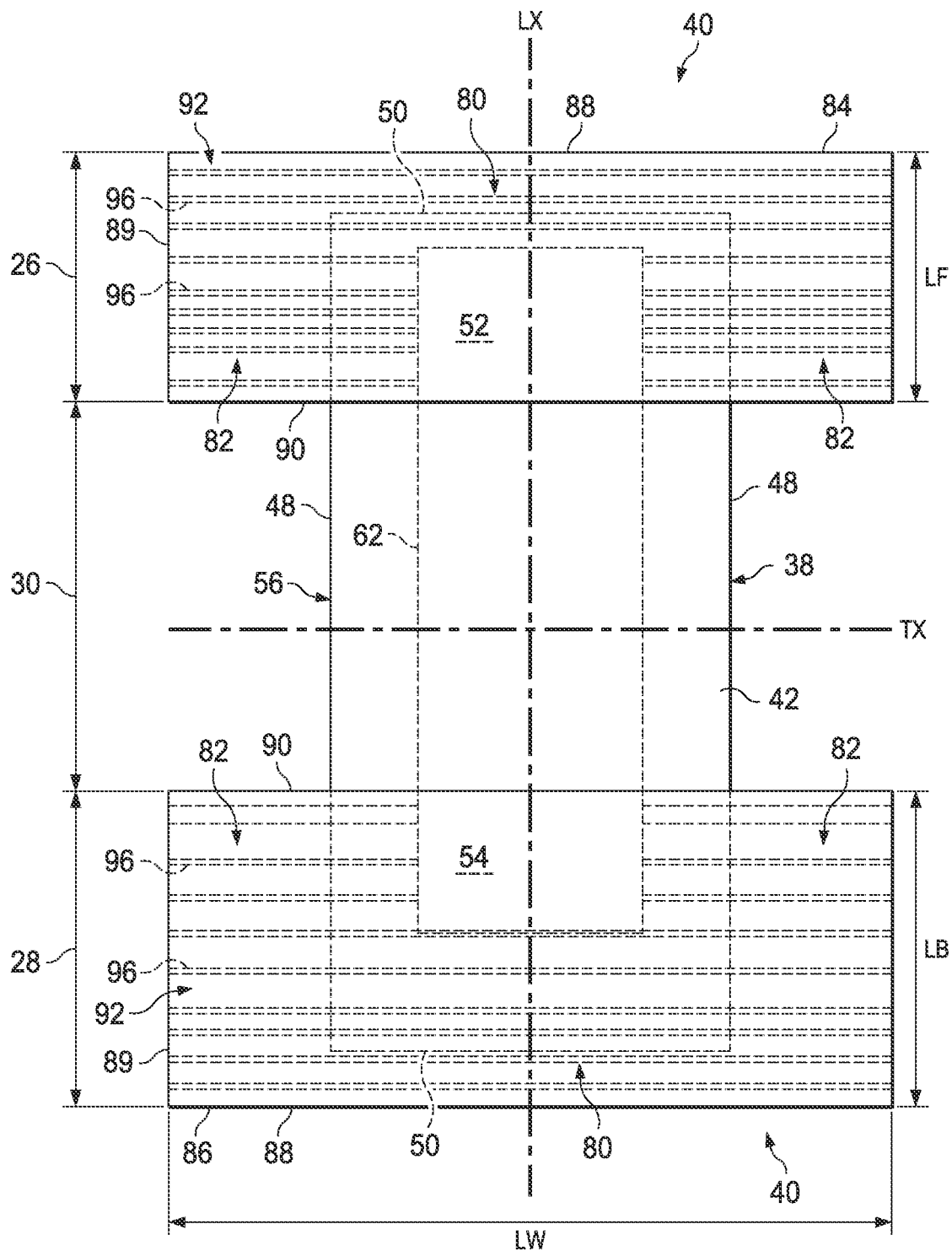
FIG. 2A is a schematic plan view of the absorbent article of FIG. 1 in a flat uncontracted condition showing the garment facing surface.
Figure 3A:
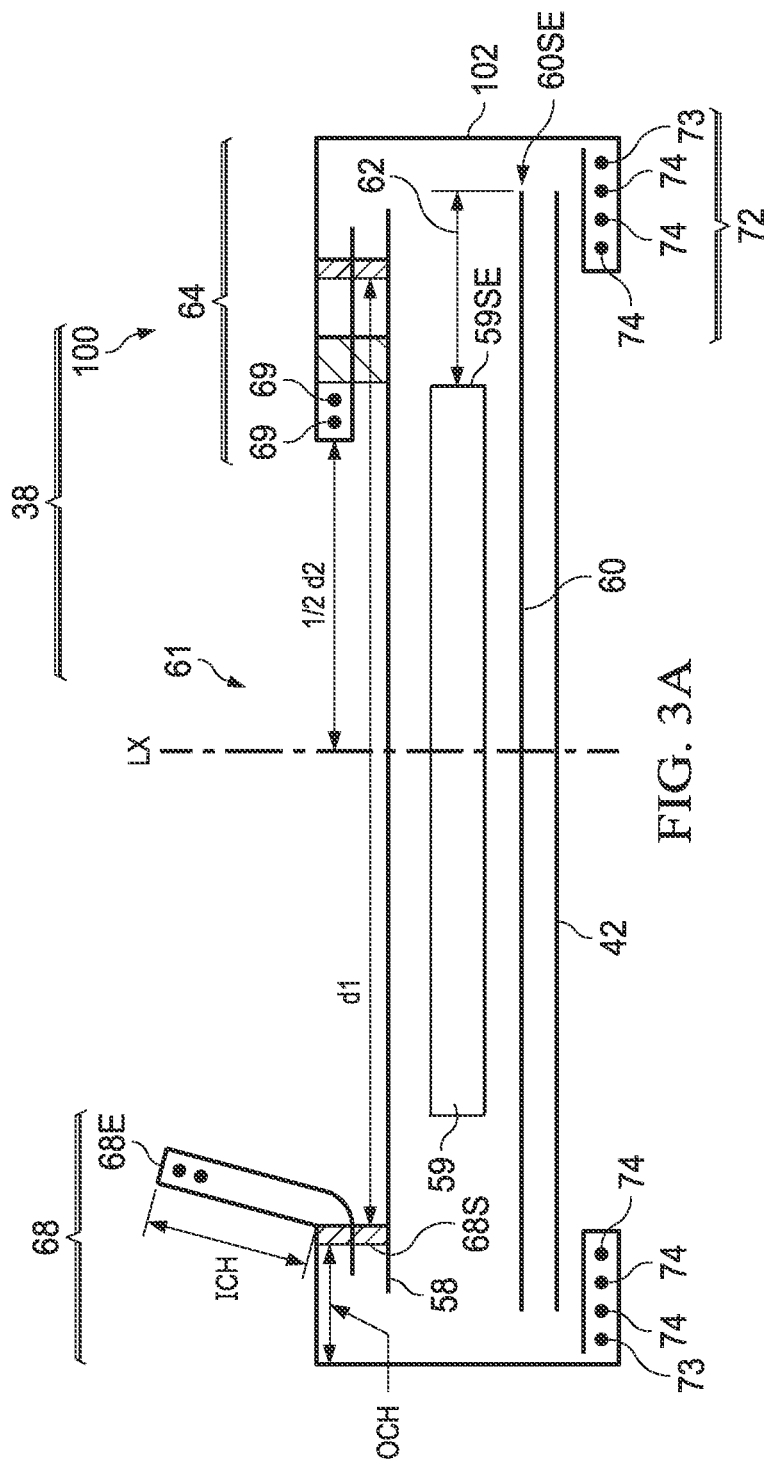
FIG. 3A is a schematic cross section view of an embodiment of the leg gasketing system of the present invention, partly taken along line TX and partly taken along line TDB of FIG. 2C.

Referring to FIG. 2A, the present article has a longitudinal centerline LX which also serves as the longitudinal axis, and a transverse centerline TX which also serves as the transverse axis. The term "proximal" refers to being closer to the transverse centerline TX, the term "distal" refers to being farther from the transverse centerline TX, the term "inward" refers to being closer to the longitudinal centerline LX, and the term "outward" refers to being farther from the longitudinal center line LX. The present article comprises an absorbent body (38) comprising a core chassis (61) and a leg gasketing system (100). Referring to FIG. 3A, the core chassis (61) comprises a liquid permeable topsheet (58); a liquid impermeable backsheet (60); an absorbent core (59) disposed between the topsheet (58) and the backsheet (60), the absorbent core (59) having a smaller dimension than the backsheet in both the longitudinal direction and the transverse direction; an outer cover (42) disposed on the garment facing side of the backsheet (60), the outer cover (42) having a greater dimension than the absorbent core (59) in both the longitudinal direction and the transverse direction, and the same or smaller dimension than the backsheet (60) in both the longitudinal direction and the transverse direction; and a pair of core side regions (62) defined as the region between the respective absorbent core side edges (59SE) and the backsheet side edges (60SE).

The topsheet (58) is generally a portion of the core chassis (61) that may be positioned at least in partial contact or close proximity to a wearer. Suitable topsheets (58) may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet (58) is generally supple, soft feeling, and non-irritating to a wearer's skin. Generally, the topsheet (58) is liquid permeable, permitting bodily fluids to readily penetrate through the thickness of the topsheet (58). One topsheet (58) useful herein is available from Fibertex NiLai, Malaysia with tradename H30501221 or FQN Hazlet NJ with tradename SB1206169. Any portion of the topsheet (58) may be coated with a lotion or skin care composition as is known in the art. Examples of suitable lotions include those described in U.S. Pat. Nos. 5,607,760; 5,609,587; 5,1005,191; and 5,643,588.

The backsheet (60) is positioned such that it extends beyond the absorbent core (59) in both the longitudinal direction and the transverse direction. The backsheet (60) may be designed to prevent the exudates absorbed by and contained within the absorbent core (59) from soiling articles that may contact the absorbent article, such as bed sheets and undergarments. Generally, the backsheet (60) is substantially water-impermeable. Suitable backsheet (60) materials include films such as those manufactured by Plaster Argentina with tradename PLBA NBBS 10-12GSM PR V1. Other suitable backsheet (60) materials may include breathable materials that permit vapors to escape from the absorbent article while still preventing exudates from passing through the backsheet (60). Exemplary breathable materials may include materials such as woven webs, nonwoven webs, composite materials such as film-coated nonwoven webs, and microporous films such as manufactured by Daika Japan with tradename MPF DKH-180 15G V7 and manufactured by Berry Nashville, TN with trademark BR-137P V13. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet including, but not limited to, surface treatments, particular film selections and processing, particular filament selections and processing, etc.

The outer cover (42) is located on the garment-facing side of the core chassis (61). The outer cover (42) may be made of a soft, non-woven material. The outer cover (42) and the backsheet (60) may be joined together by adhesive or any other suitable material or method. A particularly suitable outer cover (42) is available from Fibertex NiLai Malaysia with tradename A10160EJ-MALAYSIA and available from FQN Hazlet NJ with tradename SM1104174.

The absorbent core (59) may include an absorbent layer and an acquisition layer. The absorbent layer is the region wherein absorbent materials having a high retention capacity, such as superabsorbent polymers, are present. The absorbent layer may be substantially cellulose free.

Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet (58) and the absorbent layer. The acquisition layer may include cellulosic fibers. The absorbent layers may be disposed in plurality in the absorbent core (59). Some portions of the absorbent layers may be configured to have substantially no absorbent material to form a channel or a plurality of channels. Channels may be useful for allowing the absorbent core (59) to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

Figure 2B:
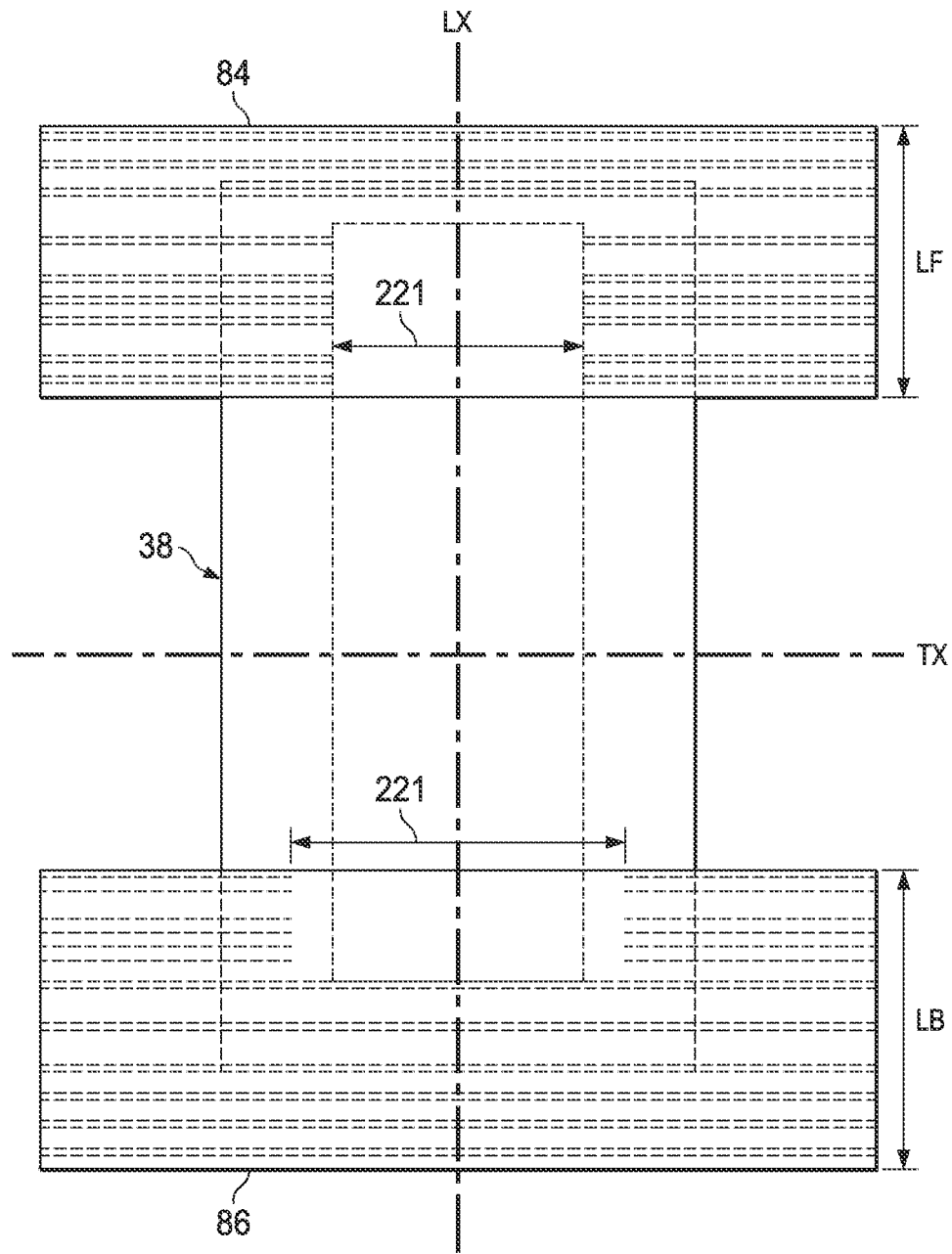
FIG. 2B is a schematic plan view of another embodiment of the absorbent article of FIG. 1 in a flat uncontracted condition showing the garment facing surface.
Figure 2C:
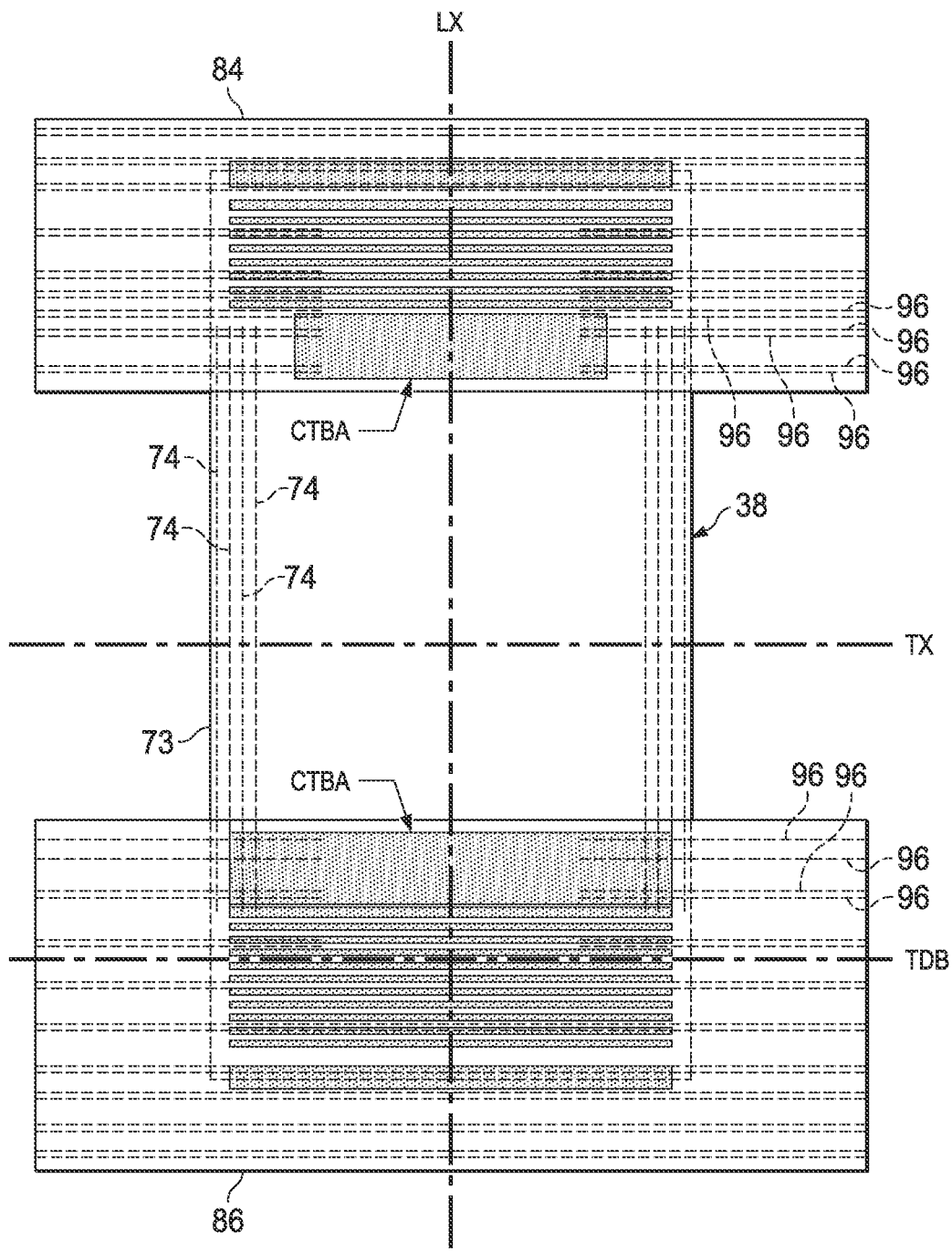
FIG. 2C is a schematic plan view of the absorbent article of FIG. 2A showing other elements of the article.
Figure 3B:
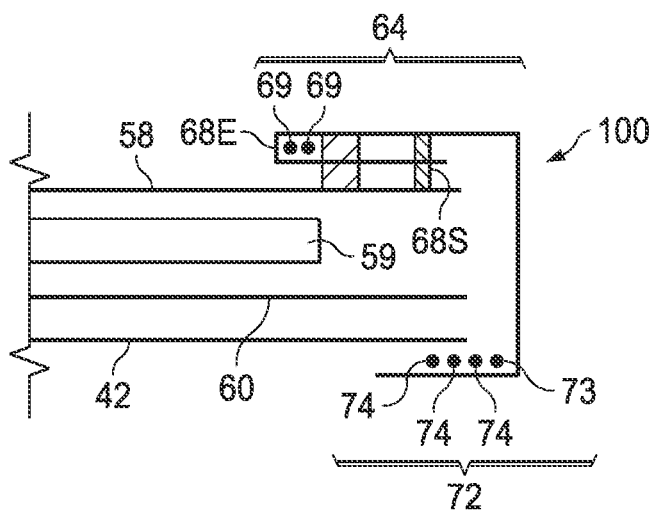
FIG. 3B is a schematic cross section view of another embodiment of the leg gasketing system of the present invention, taken along line TDB of FIG. 2C.

Referring to FIG. 3A, the left side is a schematic cross section taken along TX, while the right side is a schematic cross section taken along TDB of FIG. 2C, and with the elastic belt (40) removed. Referring to FIG. 3B, this is another schematic cross section taken along TDB and with the elastic belt (40) removed. Line TDB exists where the inner cuff (68), as detailed below, is bonded against the topsheet (58) and deactivated in elasticity. For all of FIGS. 3A-3C, the dimensions in the thickness directions are exploded. Referring to FIGS. 3A-3B, the absorbent article of the present invention comprises a leg gasketing system (100) made by a pair of water impermeable cuff material (102) disposed laterally outside and wrapping the pair of sides edges of the core chassis (61). The leg gasketing system (100) comprises a pair of wearer facing cuff regions (64) formed by inwardly extending the cuff material (102) over the wearer facing side of the core chassis (61), each wearer facing cuff region (64) comprising a longitudinally extending inner cuff sealing (68S) and a longitudinally extending inner cuff free edge (68E) positioned inward from the inner cuff sealing (68S), wherein the inner cuff sealing (68S) bonds the cuff material (102) and the topsheet (58), and an inner cuff elastic element (69) is disposed adjacent the inner cuff free edge (68E). By adjacent, what is meant is that the inner cuff elastic element (69) is disposed from about 0.5 mm to about 3 mm distant from the inner cuff free edge (68E), or from about 1 mm to about 2 mm distant from the inner cuff free edge (68E). The inner cuff sealing (68S) is a bonding means which securely bonds the cuff material (102) and the topsheet (58), such as by adhesive, by heat bond, by ultrasonic bond, or any combination thereof to provide leakage protection along the side edges of the absorbent body (38).

Referring to FIGS. 3A-3B, the leg gasketing system (100) also comprises a pair of garment facing cuff regions (72) formed by inwardly extending the cuff material (102) over the garment facing side of the core chassis (61), and a pair of outer cuff elastic elements (74) disposed on the wearer facing cuff regions (64) or the garment facing cuff regions (72), the outer cuff elastic element superposing the core side regions (62) and disposed outward from the inner cuff sealings (68S). The outer cuff elastic element (74) may be disposed on the garment facing cuff region (72). When the outer cuff elastic element (74) is disposed on the garment facing cuff region (72), the wearer facing cuff region (64) may be devoid of any outer cuff elastic element. The transverse dimension of the garment facing cuff region (72) may be from about 10 mm to about 50 mm, or from about 20 mm to about 30 mm.

Without being bound by theory, by having a pair of water impermeable cuff material (102) disposed laterally outside and wrapping the pair of sides edges of the core chassis (61) and extending inwardly into the garment facing side of the core chassis (61), the leg gasketing system (100) of the present invention may provide improved tactile softness and coverage, and provide a high quality finished appearance and underwear-like appearance. Further, by disposing the outer cuff elastic elements (74) to overlap the core side regions (62), perceived and actual leakage protection performance may be maintained. Further, these and other benefits may be achieved or enhanced by taking the configurations discussed in further detail below.

Referring to FIGS. 3A-3B, the cuff material (102) for forming the wearer facing cuff regions (64) may form a dual layer inner cuff (68) with the inner cuff elastic element (69) sandwiched therebetween, wherein the outwardly folded material is bonded against the topsheet (58) at the inner cuff sealing (68S). Alternatively, the outwardly folded material may be bonded against the cuff material (102) between the inner cuff free edge (68E) and the inner cuff sealing (68S). The inner cuff elastic element (69) may span the longitudinal length of the inner cuff (68). In other embodiments, the inner cuff elastic element (69) may span at least the longitudinal length of the inner cuff (68) within the crotch region (30). It is desirable that the inner cuff elastic element (69) exhibits sufficient elasticity such that the inner cuff (68) remains in contact with the wearer during normal wear, thereby enhancing the barrier properties of the inner cuff (68). Towards the end edges of the absorbent body (38), the inner cuff free edges (68E) may be bonded against the topsheet (58) for controlling the length of the inner cuff (68) as well as the length of the inner cuff elastic element (69) in active elasticity. Referring to FIG. 2A, line TDB exists where the inner cuff (68) is bonded against the topsheet (58) and deactivated in elasticity. Such bonding of the inner cuff (68) may be provided toward both the front and back end edges of the absorbent body (38).

Referring to FIG. 3B, the cuff material (102) for forming the garment-facing side of the garment facing cuff region (72) is defined a first garment facing fold. The cuff material (102) for forming the garment facing cuff region (72) may end at the most inward position of the garment facing cuff region (72). The side edge of the outer cover (42) may exist more inward from that of the backsheet (60). By providing the side edges of the leg gasketing system to have less material, this provides the leg gasketing system soft and breathable.

Referring to FIG. 3A, the cuff material (102) for forming the first garment facing fold may be further folded and extended outwardly to form a second garment facing fold, wherein the outer cuff elastic element (74) is sandwiched between the first garment facing fold and the second garment facing fold. When the outer cuff elastic element (74) is a plurality of elastic strands, all of the outer cuff elastic strands (74) may be sandwiched between the first garment facing fold and the second garment facing fold as in FIG. 3A, or at least one outer cuff elastic strand (74) may be sandwiched between the first garment facing fold and the second garment facing fold. Referring to FIG. 3A, the end edge of the second garment facing fold may exist beyond the side edge of the backsheet (60) and completely sandwich the outer leg elastic element (74). This may provide the side edge of the leg gasketing system lofty.

Each of the inner cuff elastic element (69) and the outer cuff elastic element (74) may be an elastic film, one or a plurality of elastic ribbons, or a plurality of elastic strands, respectively. When a plurality of elastic strands are disposed for the elastic element, those having a denier of from about 310 dtex to about 680 dtex may be disposed at an elongation of no more than about 330%. By elongation, "0% elongation" is meant the original length of the elastic member. Such denier and elongation may be suitable for providing the desired force while being less irritating to the wearer, and thus avoid red marks. When the outer cuff elastic element (74) comprises one or more elastic strands, the total number of outer cuff elastic strands (74) on one side may be at least 3. Such plurality of outer cuff elastic strands (74) may be disposed at a pitch of less than about 8 mm, or less than about 6 mm. Without being bound by theory, by having at least 3 outer cuff elastic strands (74) on each side, it is believed that good leakage prevention may be achieved with less stress against the wearer's skin.

When the outer elastic element (74) is provided in a plurality of elastic strands, the force provided by the outer cuff elastic strand (74) existing most outward is lower than that provided by the outer cuff elastic strand (74) existing most inward. For example, if there are 3 elastic strands, the most outward strand may be provided with lower force than the remaining 2 elastic strands. For example, if there are 4 elastic strands, the 2 outward strands may be provided with lower force than the remaining 2 elastic strands. Without being bound by theory, it is believed that by providing the outward strands with lower force, the stress against the wearer is decreased and a soft fit is achieved while maintaining leakage prevention.

Referring to FIGS. 3A-3B, there may be at least 3 outer cuff elastic strands (74) on the garment facing cuff region (72). Such configurations provide a band like appearance on the garment facing side of the absorbent article. This is advantageous in providing an under-garment like appearance to the absorbent article. Referring to FIG. 3A, there are at least 2 layers of material between the wearer and the outer cuff elastic element (74), wherein the layers of material are selected from the group consisting of the cuff material (102), the topsheet (58), the backsheet (60), and the outer cover (42). By having at least 2 layers of material between the wearer and the outer cuff elastic element (74), this prevents the outer cuff elastic element (74) to cause irritation or red marks against the wearer's inner thighs, which is typically a sensitive area of skin.

Referring to FIGS. 3A-3B, the leg gasketing system (100) may further comprise a side edge elastic strand (73) wherein the side edge elastic strand (73) is disposed outward from the backsheet (60). The side edge elastic strand (73) may exist about 1-2 mm away from the outward edge of the cuff material (102). There may be at least 1, or 1-2 side edge elastic strands (73) on each side. Without being bound by theory, it is believed that by disposing the side edge elastic strand (73) at the most outward portion of the leg gasketing system (100), this provides structure to the side edges of the leg gasketing system (100) while avoiding the backsheet (60) to exist in this position. When the backsheet (60) is extended to the most outward portion of the leg gasketing system (100), there is tendency to provide a stiff feeling against the wearer's thigh.

Referring to FIGS. 2A-2B, the absorbent article of the present invention may have each front and back belt (84, 86) formed by a plurality of elastic bodies (96) running in the transverse direction sandwiched between an inner sheet (94) and an outer sheet (92). Each front belt (84) and back belt (86) has transversely continuous proximal and distal edges (90, 88), the proximal edge (90) being located closer than the distal edge (88) relative to the longitudinal center of the article. The elastic belt (40) formed by the front and back belt (84, 86) of the present invention acts to dynamically create fitment forces and to distribute the forces dynamically generated during wear. Elasticity around the leg opening may be provided by the combination of elasticity from the front elastic belt (84), the back elastic belt (86), and the leg gasketing system (100).

The longitudinal length of the backsheet (36) and the outer cover layer (42) may be the same, or may be varied. For example, the outer cover layer (42) may have a shorter length compared to that of the backsheet (36), such that the outer cover layer (42) is devoid where the absorbent body (38) overlaps the elastic belt (40). By such configuration, the elastic belt may have better breathability. Further, such configuration may provide cost saving. The transverse width of the backsheet (36) and the outer cover layer (42) may be the same, or may be varied. For example, the backsheet (36) may have a shorter transverse width compared to that of the outer cover layer (42). By such configuration, the longitudinal side edges (48) of the crotch panel (56), which make part of the leg openings, may have better breathability. Further, such configuration may provide cost saving. The backsheet (36) may extend to the transversely extending end edges (50) of the absorbent body (38) for providing leakage prevention.

Referring to FIG. 2A-2B, the longitudinal length LB of the back elastic belt (86) and the longitudinal length LF of the front elastic belt (84) may be provided the same, or the back elastic belt (86) may have a greater longitudinal length LB. When the wearable article is assembled to form the waist opening and the leg openings, the wearable article (20) is folded along the transverse centerline T1 such that the front distal edge (88) is aligned with the back distal edge (88). The front side edge (89) is also aligned with a portion of the back side edge (89). Then the front elastic belt (84) and the back elastic belt (86) are joined at the front and back side edges (89) at the seams (32). The front and back proximal edges (90), however, may not be aligned to one another. The back proximal edge (90) may be disposed longitudinally closer than the front proximal edge (90) relative to the transverse center line T1 such that the proximal portion of the back side panel (82) extends toward the crotch panel (56) of the main body (38) beyond the front proximal edge (90). The side edge of the proximal portion of the back side panel (82) may not be joined to anywhere and free from attachment. Thus, the proximal portion of the back side panel (82) provides a buttock cover (95) (not shown).

The front elastic belt (84) and back elastic belt (86) are configured to impart elasticity to the belt (40). The belt elastic bodies (96) may extend in the transverse direction to provide a ring like elastic belt (40) when the front belt (84) and the back belt (86) are joined. At least some of the elastic bodies (96) extend in the transverse direction substantially parallel to each other. All of the elastic members (96) may extend in the transverse direction substantially parallel to each other. Such an article may be economically made. At least 10%, or at least from about 15% to not more than about 70%, of the front and back belts, from the waist opening in the longitudinal direction], may be in active elasticity along the entire transverse dimension LW of the front and back belts (84, 86). For each front and back elastic belt (84, 86), the region overlapping the front and/or back waist panel (52, 54) of the absorbent body (38) may be removed of its elastic activity. Such region removed of elastic activity is referred to herein as the "elastic cut window", and the remainder of the intact elastic member capable of imparting elasticity is defined as the "effective length of elasticity of an elastic member".

The tensile stress (N/m) of the entirety of the front and back elastic belts (84, 86), respectively, may be profiled in order to provide the functional benefits of the present invention, such as ease of stretch and application, while also maintaining certain force during wear, to prevent the article from sagging after loading. When the elasticity of the front and back elastic belts (84, 86) are provided by a plurality of elastic members (96) running in the transverse direction, the tensile stress may be adjusted by one or more of the following methods; 1) elongation rate of the elastic member (96); 2) density (dtex) of the elastic member (96); 3) longitudinal pitch of multiple elastic members (96); and 4) effective length of elasticity of the elastic member (96) in the transverse direction. By elongation, "0% elongation" is meant the original length of the elastic member.

Figure 4:
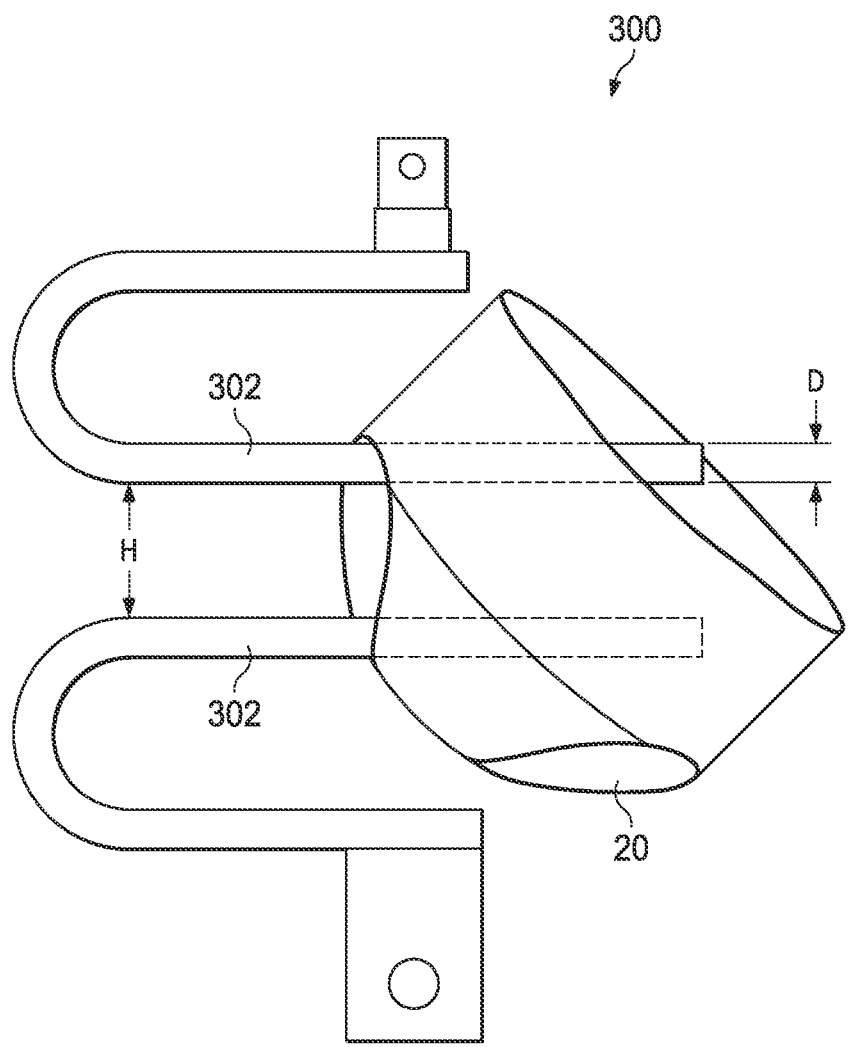
FIG. 4 is a schematic view of an example of a hanger-type sample holding fixture according to the "Leg Opening Measurement" herein.

Referring to FIGS. 1 and 4, the absorbent article of the present invention may have a Worn Leg Opening (WLO) and Minimum Leg Opening (MLO) as measured by the Leg Opening Measurement below. The Worn Leg Opening (WLO) is intended to measure the greatest circumferential dimension of the leg opening worn by the wearer under reasonable level of tension. Namely, the Worn Leg Opening (WLO) represents the circumferential dimension of the leg opening worn by the wearer of intended largest size. The Worn Leg Opening (WLO) may be from about 300 mm to about 450 mm for baby diapers of sizes 3 (M) to 5 (XL) suitable for babies and toddlers having a weight of from about 6 kg to about 20 kg. The Minimum Leg Opening (MLO) is intended to measure the smallest circumferential dimension of the leg opening worn by the wearer under hardly any tension. Namely, the Minimum Leg Opening (MLO) represents the circumferential dimension of the leg opening worn by the wearer of intended smallest size. The Minimum Leg Opening (MLO) may be from about 225 mm to about 300 mm for baby diapers of sizes 3 (M) to 5 (XL) suitable for babies and toddlers having a weight of from about 6 kg to about 20 kg. The ratio of WLO/MLO may be from about 1.5 to about 1.7.

By providing the aforementioned Worn Leg Opening (WLO), Minimum Leg Opening (MLO), and ratio thereof, the leg gasketing system of the present invention provides a secure sense of leg gasketing and prevent leakage, while avoiding red marks and without overly tight feeling, across a greater percentage of wearers of the intended size. A number of factors may be considered for providing the suitable Worn Leg Opening (WLO), Minimum Leg Opening (MLO), and ratio thereof, of the present invention. Such factors are provided below.

1) The joining between the garment facing cuff region (72) of the leg gasketing system (100) and the belt may be adjusted. The front and/or back belt (84, 86) and the absorbent body (38) may be joined in a manner such that at least a portion of the outer cuff elastic element (74) in active elasticity is left unjoined to the front and/or back belt (84, 86). For example, referring to FIG. 2C, the garment facing cuff region (72) comprising the outer cuff elastic element (74) in active elasticity may be joined so as to only partly superpose, or not superpose the front belt (84) and/or the back belt (86). The region of joining between the garment facing cuff region (72) and the belt may be controlled by configuring the adhesive region (CTBA) as shown in FIG. 2C. When the outer cuff elastic element (74) is provided in the plurality of elastic strands, at least the most inwardly disposed outer cuff elastic strand (74) may superpose the front belt (84) or the back belt (86). Referring to FIG. 2C, the garment facing cuff region (72) is joined so that only 2 inwardly disposed outer cuff elastic strands (74) superpose the back belt (86), while there are no outer cuff elastic strands (74) superposing the front belt (84). The adhesive region (CTBA) for joining the garment facing cuff region (72) and the belt may be provided in a dimension so as to at least cover the non-elastic region of the elastic belt (40). By providing the joining of the leg gasketing system (100) and elastic belt (40) in such way, sufficient leg opening is secured without compromise to the fit of the crotch region (30).

Still referring to FIG. 2C, the elastic bodies (96) of the back belt (86) may at least partially superpose the outer elastic cuff member (74) of the leg gasketing system (100) in order to transmit the tensile force. The elastic bodies (86) of the back belt superposing the outer elastic cuff member (74) may be in active elasticity for at least about 10 mm inwardly from the outer elastic cuff member (74). By having the tensile force of the leg gasketing system (100) transmittable to the back belt (86), a smooth leg opening circumference is made, which further helps shape the absorbent body (38) to follow the wearer's hip.

2) The dimension of the elastic cut window of the front and/or back belt (84, 86) may be adjusted for providing a non-elastic region at least partially superposing the absorbent core in the thickness direction. The non-elastic region may be provided in different transverse dimension between the front belt and the back belt as in FIG. 2B. The transverse dimension of the non-elastic region (221) in the greatest dimension is referred to as a maximum transverse dimension. The back belt may comprise a non-elastic region (221) having a maximum transverse dimension, wherein the maximum transverse dimension of the non-elastic region (221) of the back belt may be from about 50% to about 100% of the transverse dimension of the absorbent body. As a result, the non-elastic region (221) of the back belt (86) may be provided greater than that of the front belt (84). By providing a relatively large non-elastic region (221) for the back belt, this provides improved buttock coverage.

3) The longitudinal length of the front belt (LF) and the back belt (LB), and the spacing between the front belt (84) and the back belt (86) may be adjusted. The longitudinal length of the back belt (LB) may be from about 110% to about 130% of that of the front belt (LF).

The dimensions of the inner cuff (68) and the remainder of the leg gasketing system (100) may be carefully coordinated in order to provide good leakage prevention. Referring to FIG. 3A, inner cuff (68) has an inner cuff height (ICH) which is the transverse dimension between the inner cuff sealing (68S) to the inner cuff free edge (68E), the garment facing cuff region (72) has an outer cuff height (OCH) which is the transverse dimension between the inner cuff sealing (68S) to the side edge of the leg gasketing system (100), wherein the inner cuff height (ICH) is greater than the outer cuff height (OCH). The inner cuff height (ICH) may be greater than the outer cuff height (OCH) by from about 2 mm to about 12 mm. By providing the inner cuff height (ICH) slightly greater than the outer cuff height (OCH), there is an appropriate amount of force provided against the wearer during wear, while preventing the inner cuff (68) from extending out in the leg opening.

Referring to FIG. 3A, the absorbent article of the present invention may have a void space which is the sum of 2 inner cuff heights (ICH) and the transverse dimension (d1) between the pair of inner cuff sealings, wherein the void space may be from about 150 mm to about 250 mm, or from about 200 mm to about 230 mm. By having an appropriate void space, the absorbent article may have enough containment, while also staying in close proximity of the wearer while it is applied.

Referring to FIG. 3A, the absorbent article of the present invention may have a cuff spacing which is the transverse dimension (d2) between the pair of inner cuff free edges (68E) when the inner cuffs are completely laid flat on the core chassis, wherein the cuff spacing may be from about 70 mm to about 140 mm, or from about 80 mm to about 130 mm, or from about 84 mm to about 104 mm.

The dimensions of the absorbent body (38) may further enhance the function of the leg gasketing system (100) of the present invention. The absorbent body (38) may have a transverse dimension of from about 180 mm to about 230 mm, or from about 204 mm to about 216 mm. The transverse dimension of the absorbent body (38) is defined as the smallest dimension of the absorbent body (38) parallel to the transverse axis (TX). When the absorbent body (38) is rectangular as in FIGS. 2A-2B, the transverse dimension is the same for the entire longitudinal length of the absorbent body (38).

The cuff material (102) may be made from a substantially liquid impervious material. The material may be an SMS nonwoven or an SMMS nonwoven material, or a nonwoven component layer comprising fine fibers having an average diameter of less than 1 micron. One useful combination of nonwoven fabric webs may include spunbond, meltblown, spunbond ("SMS") webs comprising outer layers of spunbond thermoplastics (e.g., polyolefins) and an interior layer of meltblown thermoplastics. Suitable cuff material (102) useful herein include include those of SMS type available from Toray Polytech Nantong China with tradename LIVSEN SMS 13, available from FQN Hazlet NJ with tradename SM15009270, and available from Fibertex Aalborg Denmark with tradename B10160HS.

While made from the same cuff material (102), the wearer facing cuff region (64) and the garment facing cuff region (72) may be treated, by region or in part of a region, with a lotion or a hydrophobic surface coating to provide various physical properties. The cuff material (102) may have a hydrostatic head of greater than about 2 mbar, or greater than about 3 mbar, or greater than about 4 mbar. The cuff material (102) may have a hydrostatic head of less than about 200 mbar, or less than about 100 mbar, or less than about 75 mbar, or less than about 50 mbar, or less than about 25 mbar, or less than about 15 mbar. The cuff material (102) may have an opacity of from about 15% to about 50% hunter opacity, or from about 20% to about 45% hunter opacity. The cuff material (102) may have an opacity of from about 45% to about 75% hunter opacity; or from about 50% to about 70% hunter opacity. The cuff material (102) may have an air permeability of less than about 50 m3/m2/min; or less than about 45 m3/m2/min. The cuff material (102) may have an air permeability of greater than about 5 m3/m2/min; or greater than about 10 m3/m2/min; or greater than about 15 m3/m2/min; or greater than about 20 m3/m2/min.

Leg Opening Measurement

The Worn Leg Opening (WLO) and the Minimum Leg Opening (MLO) may be obtained for articles which are the pant type, namely wherein the elastic belt (40) is an elastic belt extending transversely from the front and back regions of the absorbent body and seamed with each other at the pair of transverse edges. The Worn Leg Opening (WLO) and the Minimum Leg Opening (MLO) is obtained when a certain force is applied to the leg opening.

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions.

The tensile tester is fitted with hanger-type sample holding fixtures (300) as shown in FIG. 4. Each fixture comprises a rigid linear rubber-coated horizontal bar section (302) to prevent sample slippage during testing. The outer bar diameter (including the rubber coating) of the horizontal bar sections (302) is 10.0 mm. The central axes of the horizontal bar sections (302) are configured to remain parallel and in the same vertical plane throughout the test procedure.

The gauge circumference is determined by the following equation:

Gauge Circumference=2×(H+D+πD/2)

where H is the vertical gap between the horizontal bar sections (302), and D is the outer diameter of the bar. All testing is performed in a room maintained at 23±2° C. and 50±5% relative humidity. The instrument is set up to go through the following steps:

| | |
|---|---|
| Crosshead Speed: | 254.0 mm/min |
| Final Load Point: | 12N |
| Hold Time | 0 |
| Number of Cycles | 1 |
| Data Acquisition Rate | 50 Hz |

A sample article is inserted onto the upper horizontal bar section (302) from one leg opening while positioning the article with the crotch side down, so that the bar passes through the one leg opening and waist opening of the article. The crosshead is raised until the specimen hangs above the lower bar and does not touch lower bar (302). The load cell is reset to zero and the crosshead is lowered to enable the lower bar (302) to be inserted through the leg opening without stretching the article. The sample is adjusted so that the proximal edge of the side seam and outer cuff elastic element(s) are on the same vertical axis as the instrument load cell. The crosshead is raised slowly while the sample is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 12N is attained, then the crosshead immediately returns to the Initial Gauge Circumference at the same speed. The circumference at 8N during the load (extension) segment of the test and the circumference at 0.1N during the unload (contraction) segment of the test are recorded.

The circumference at 8N is defined as the Worn Leg Opening (WLO). The circumference at 0.1N is defined as Minimum Leg Opening (MLO). Five samples are analyzed and their average Worn Leg Opening (WLO) and average Minimum Leg Opening (MLO) on both left and right leg openings and are calculated and reported to the nearest 1 mm.

Opacity Method

Opacity is measured using a 0° illumination/45° detection, circumferential optical geometry, spectrophotometer with a computer interface such as the HunterLab LabScan XE running Universal Software (available from Hunter Associates Laboratory Inc., Reston, VA) or equivalent instrument. Instrument calibration and measurements are made using the standard white and black calibration plates provided by the vendor. All testing is performed in a room maintained at 23±2° C. and 50±2% relative humidity.

The spectrophotometer is configured for the XYZ color scale, D65 illuminant, 10° standard observers, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2° C. and 50%±2% relative humidity for two hours prior to testing. To obtain a cuff material specimen, the article is stretched flat on a bench, body facing surface upward, and the total longitudinal length of the article is measured. A testing site on the inner cuff (68) is selected at the longitudinal midpoint of the article. Using scissors, a test specimen is cut 60 mm long by the entire height of the inner cuff (68) centered at the longitudinal midpoint of the inner cuff (68). In like fashion, specimens are prepared from the inner cuffs (68) on the right side of the article. Any elastic members are removed.

The specimen is placed over the measurement port. The specimen should completely cover the port with the surface corresponding to the inner-facing surface of the inner cuff (68) directed toward the port. The specimen is gently extended until taut in its longitudinal direction so that the specimen lies flat against the port plate. Adhesive tape is applied to secure the specimen to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

Opacity=($Y$ value$_{(black\ backing)}$/$Y$ value$_{(white\ backing)}$)×100

Specimens from five identical articles (10 inner cuffs (68) (5 left and 5 right)) are analyzed and their opacity results recorded. The average opacity is calculated and reported to the nearest 0.01%.

Air Permeability Test

Air permeability is tested using a TexTest FX3300 Air Permeability Tester (available from Advanced Testing Instruments, Greer, SC) with a custom made 1 cm$^2$ circular aperture (also available from Advanced Testing Instruments) or equivalent instrument. The instrument is calibrated according to the manufacturer's procedures. All testing is performed in a room maintained at 23° C.±2° C. and 50±2% relative humidity.

The articles are pre-conditioned at 23° C.±2° C. and 50%±2% relative humidity for two hours prior to testing. To obtain a specimen, the article is stretched flat on a bench, body facing surface upward, and the total longitudinal length of the article is measured. A testing site on the inner cuff (68) is selected at the longitudinal midpoint of the article. Using scissors, a test specimen is cut 30 mm long by the entire height of the inner cuff (68) centered at the longitudinal midpoint of the left cuff. In like fashion, specimens are prepared from the inner cuffs (68) on the right side of the article. Any elastic members are removed.

The specimen is centered over the measurement port. The specimen should completely cover the port with the surface corresponding to the inward-facing surface of the inner cuff (68) directed toward the port. The specimen is gently extended in its longitudinal direction until taut so that the specimen lies flat across the port. Adhesive tape is applied to secure the specimen across the port in its extended state for testing. Tape should not cover any portion of the measurement port. The test pressure is set to allow air to pass through the specimen. For non-woven specimen the pressure is set for 125 Pa and for specimen containing films 2125 Pa is used. The sample ring is closed and the measuring range is adjusted until the range indicator shows green to indicate that the measurement is within the accepted limits of the instrument. The air permeability is recorded to the nearest 0.1 m$^3$/m$^2$/min.

Hydrostatic Head Test

Hydrostatic head is tested using a TexTest FX3000 Hydrostatic Head Tester (available from Advanced Testing Instruments, Greer, SC) with a custom made 1.5 cm$^2$ circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2° C. and about 50%±2% relative humidity.

Precondition the articles at about 23° C.±2° C. and about 50%±2% relative humidity for two hours prior to testing. To obtain a specimen, lay the article stretched flat on a bench, body facing surface upward, and measure the total longitudinal length of the article. Select a testing site on the inner cuff (68) at the longitudinal midpoint of the article. Using scissors cut a test specimen 70 mm long by the entire height of the inner cuff (68) centered at the longitudinal midpoint on both the left and right sides. Any elastic members are removed.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the specimen lies flat against the upper test plate. Adhesive tape is applied to secure the specimen to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff (68) specimens) are analyzed and their hydrostatic head results recorded. Calculate and report the average hydrostatic head report to the nearest 0.1 mbar.

EXAMPLES

Examples 1-2 and Comparative Examples 1-2

Example 1 is an absorbent article of Size 4 having internal prototype number 2021040210922022N0-C. Example 1 has an overall configuration of FIGS. 2A and 2C, leg gasketing system configuration of FIG. 3A, and structural elements and dimensions as in Table 1 below. The number of elastic strands are for one side only. The cuff material is a nonwoven material of SMS type available from Toray Polytech Nantong China with tradename LIVSEN SMS 13 as cuff material, Example 2 is an absorbent article of Size 4 having internal prototype number 2021040210922022N0-D. Example 2 has an overall configuration of FIG. 2B, leg gasketing system configuration of FIG. 3B, joining of the leg gasketing system and elastic belt as in FIG. 2C, and structural elements and dimensions as in Table 1 below. The number of elastic strands are for one side only. The cuff material is a nonwoven material of SMS type available from Toray Polytech Nantong China with tradename LIVSEN SMS 13 as cuff material.

Comparative Example 1 is an absorbent article of Size 4 having internal prototype number 2021040210922022N0-B. Comparative Example 1 replaced the leg gasketing system of Comparative Example 2. Comparative Example 1 has an overall configuration of FIG. 2A, leg gasketing system configurations of FIG. 3A, and structural elements and dimensions as in Table 1 below. The number of elastic strands are for one side only. The cuff material is a nonwoven material of SMS type available from Toray Polytech Nantong China with tradename LIVSEN SMS 13 as cuff material.

Figure 3C:
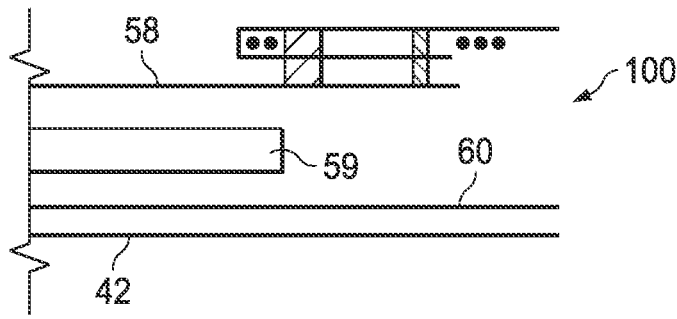
FIG. 3C is a schematic cross section view of a leg gasketing system of the prior art.

Comparative Example 2 is "Pampers Sarasara Care Pants" Size 4 available from P&G in the Japanese market in 2020 having Lot No. 0151202271 and having a leg gasketing system configuration of FIG. 3C, and having structural elements and dimensions as in Table 1 below. The number of elastic strands are for one side only.

TABLE 1

| Example | 1 | 2 | Comparative 1 | Comparative 2 |
|---|---|---|---|---|
| Worn Leg Opening (WLO) (mm) | 385 | 394 | 350 | 385 |
| Minimum Leg Opening (MLO) (mm) | 244 | 255 | 218 | 268 |
| Ratio of WLO/MLO | 1.58 | 1.55 | 1.60 | 1.44 |
| Absorbent body transverse dimension (mm) | 216 | 216 | 216 | 206 |
| Belt length Front/Back (mm) | 121/156 | 121/136 | 121/156 | 121/156 |
| Belt to belt distance (mm) | 193 | 213 | 193 | 193 |
| CTBA width of front belt superposing outer cuff elastic member (mm) | 163 | 163 | 196 | 186 |
| Backsheet width (mm) | 198 | 198 | 198 | 198 |
| Outer cover width (mm) | 198 | 198 | 198 | 198 |
| Inner cuff height (mm) | 32 | 32 | 32 | 34 |
| Outer cuff height (mm) | 28 | 28 | 28 | 28 |
| Cuff spacing (mm) | 84 | 84 | 84 | 76 |
| Void space (mm) | 212 | 212 | 212 | 212 |
| Outer cuff elastic disposition | Garment facing side | Garment facing side | Garment facing side | Wearer facing side |
| Number of outer cuff elastic strands/side | 4 | 4 | 4 | 3 |
| Pitch of outer cuff elastic strands (mm) | 6 | 6 | 6 | 3 |
| Higher force outer cuff elastic strand: #/dtex/elongation | 4/470/240% | 4/470/240% | 4/470/240% | 3/540/300% |
| Lower force outer cuff elastic strand: #/dtex/elongation | NA | NA | NA | NA |
| Number of side edge elastic strands | 1 | 1 | 1 | 0 |
| First garment facing fold transverse dimension (mm) | 25 | 30 | 25 | NA |
| Second garment facing fold transverse dimension (mm) | 22 | NA | 22 | NA |

Comparative Example 1 replaced the leg gasketing system of the present invention on the product of Comparative Example 2. Comparative Example 1 was not acceptable as not having the minimum Worn Leg Opening (WLO) (mm) required of a Size 4 product, thus risking red marking and compromised softness.

Compared to Comparative Example 1, Examples 1 and 2 have acceptable minimum Worn Leg Opening (WLO) (mm) required of a Size 4 product. Compared to Comparative Example 2, Examples 1 and 2 have an improved and favorable ratio of WLO/MLO. Examples 1 and 2 provide a leg gasketing system with improved softness, coverage, and leakage prevention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a skin facing side, a garment facing side, a longitudinal axis, a transverse axis, a pair of longitudinally extending side edges, and a pair of transversely extending end edges, the absorbent article comprising an absorbent body, a front belt joined to the front side of the absorbent body, a back belt joined to the back side of the absorbent body, and the transverse edges of the front belt and the back belt are joined by a seam to form a waist opening and two leg openings, each front belt and back belt formed by a plurality of elastic bodies running in the transverse direction sandwiched between an inner sheet and an outer sheet;

the absorbent body comprising:
      a core chassis comprising:
         a liquid permeable topsheet;
         a liquid impermeable backsheet;
         an absorbent core disposed between the topsheet and the backsheet, the absorbent core having a smaller dimension than the backsheet in both the longitudinal direction and the transverse direction;
         an outer cover disposed on a garment facing side of the backsheet, the outer cover having a greater dimension than the absorbent core in the transverse direction, and the same or smaller dimension than the backsheet in both the longitudinal direction and the transverse direction; and a pair of core side regions defined as the region between absorbent core side edges and the backsheet side edges; and a leg gasketing system made by a pair of water impermeable cuff material disposed laterally outside and wrapping the pair of sides edges of the core chassis, the leg gasketing system comprising:

a pair of wearer facing cuff regions formed by inwardly extending the cuff material over a wearer facing side of the core chassis; each of the pair of wearer facing cuff regions comprise a longitudinally extending inner cuff sealing and a longitudinally extending inner cuff free edge positioned inward from the inner cuff sealing, wherein the inner cuff sealing bonds the cuff material and the topsheet, and an inner cuff elastic element is disposed adjacent the inner cuff free edge;

a pair of garment facing cuff regions formed by inwardly extending the cuff material over a garment facing side of the core chassis, and a pair of outer cuff elastic elements disposed on the garment facing cuff regions, each outer cuff elastic element disposed so as to superpose the core side regions and so as to superpose the inner cuff sealings or outward thereof; and wherein the garment facing cuff regions are formed by the cuff material extending inwardly from a first fold line to define a first cuff garment facing fold and the cuff material extending outwardly from a second fold line to define a second cuff garment facing fold;

wherein the outer cuff elastic element is sandwiched between the first garment facing fold and the second garment facing fold; and wherein the second cuff garment facing fold is sandwiched between the outer cuff elastic element and the garment facing side of the core chassis; and wherein the absorbent article has a Worn Leg Opening (WLO) of from 300 mm to 450 mm, a Minimum Leg Opening (MLO) of from 225 mm to 300 mm, and a ratio of WLO/MLO of from 1.5 to 1.7.

2. The absorbent article of claim 1, wherein each outer cuff elastic element comprises one or more elastic strands, wherein the total number of outer cuff elastic strands on one side is at least 3.

3. The absorbent article of claim 2, wherein the force provided by the outer cuff elastic strand disposed most outward is lower than that provided by the outer cuff elastic strand disposed most inward.

4. The absorbent article of claim 3, wherein any outer cuff elastic strand is disposed at an elongation of no more than 330%.

5. The absorbent article of claim 4, wherein any outer cuff elastic strand has a denier of no more than 680 dtex.

6. The absorbent article of claim 1, wherein the transverse dimension of the garment facing cuff region is from 10 mm to 50 mm.

7. The absorbent article of claim 1, wherein the inner cuff has an inner cuff height which is the transverse dimension between the inner cuff sealing to the inner cuff free edge, the garment facing cuff region has an outer cuff height which is the transverse dimension between the inner cuff sealing to the side edge of the leg gasketing system, wherein the inner cuff height is greater than the outer cuff height.

8. The absorbent article of claim 7, wherein the inner cuff height is greater than the outer cuff height by from 2 mm to 12 mm.

9. The absorbent article of claim 1, comprising a void space which is the sum of 2 inner cuff heights and the transverse dimension between the pair of inner cuff sealings, wherein the void space is from 150 mm to 250 mm.

10. The absorbent article of claim 1, comprising a cuff spacing which is the transverse dimension between the pair of inner cuff end edges when the inner cuffs are completely laid flat on the core chassis, wherein the cuff spacing is from 70 mm to 140 mm.

11. The absorbent article of claim 1, wherein the absorbent body has a transverse dimension of from 180 mm to 230 mm.

12. The absorbent article of claim 1, wherein each side of the leg gasketing system further comprises a side edge elastic strand wherein the side edge elastic strand is disposed outward from the backsheet.

13. The absorbent article of claim 1, wherein the back belt and the leg gasketing system are configured such that the tensile force of the leg gasketing system is transmittable to the back belt.

* * * * *